United States Patent [19]
Andersen et al.

[11] Patent Number: 5,745,034
[45] Date of Patent: *Apr. 28, 1998

[54] PROVIDING AN ALARM IN RESPONSE TO A DETERMINATION THAT A PERSON MAY HAVE SUDDENLY EXPERIENCED FEAR

[76] Inventors: Stig Lundegaard Andersen, Havrevej 7, Esbonderup, Graested 3230, Denmark; Jens Ole Sorensen, P.O. Box 221, North Side, Grand Cayman, Cayman Islands

[*] Notice: The term of this patent shall not extend beyond the expiration date of Pat. No. 5,568,126.

[21] Appl. No.: 793,881
[22] PCT Filed: Jul. 8, 1996
[86] PCT No.: PCT/IB96/01016
§ 371 Date: Mar. 10, 1997
§ 102(e) Date: Mar. 10, 1997
[87] PCT Pub. No.: WO97/03426
PCT Pub. Date: Jan. 30, 1997

Related U.S. Application Data

[63] Continuation-in-part of Ser. No. 500,235, Jul. 10, 1995, Pat. No. 5,568,126.
[51] Int. Cl.[6] .................................................. G08B 21/00
[52] U.S. Cl. .......................... 340/574; 340/573; 340/691
[58] Field of Search .............................. 340/573, 574, 340/691; 364/419.2

[56] References Cited

U.S. PATENT DOCUMENTS

| | | | |
|---|---|---|---|
| 3,885,090 | 5/1975 | Rosenbaum | 360/5 |
| 4,100,536 | 7/1978 | Ball et al. | 340/574 |
| 4,665,385 | 5/1987 | Henderson | 340/539 |
| 4,829,285 | 5/1989 | Brand et al. | 340/573 |
| 4,867,442 | 9/1989 | Matthews | 482/8 |
| 4,952,928 | 8/1990 | Carroll et al. | 340/825.54 |
| 5,243,993 | 9/1993 | Alexander et al. | 128/707 |
| 5,282,474 | 2/1994 | Valdes Sosa et al. | 128/670 |
| 5,295,491 | 3/1994 | Gevins | 128/731 |
| 5,299,118 | 3/1994 | Martens et al. | 364/413.05 |
| 5,306,293 | 4/1994 | Zacouto | 607/671 |
| 5,327,899 | 7/1994 | Harris et al. | 128/671 |
| 5,410,739 | 4/1995 | Hart | 455/66 |

*Primary Examiner*—Glen Swann
*Attorney, Agent, or Firm*—Edward W. Callan

[57] ABSTRACT

A computer system processes physiological data signals provided by a physiological-condition monitoring system to determine whether the person may have suddenly experienced fear by comparing the monitored physiological data with stored stress profile data for the person that is based upon measurements of the monitored physiological conditions of the person during situations of stress and/or upon statistical classification in view of a combination of predetermined characteristics of the person. When such processing by the computer system determines that the person may have suddenly experienced fear, the computer system activates an alarm indicator. The computer system includes a neural network for modifying the stored stress profile data in response to an input signal indicating that the computer system provided a false alarm indication. The surrounding conditions that may have caused the determination of probable fear are recorded and transmitted to a remote location.

23 Claims, 2 Drawing Sheets

5,745,034

PROVIDING AN ALARM IN RESPONSE TO A DETERMINATION THAT A PERSON MAY HAVE SUDDENLY EXPERIENCED FEAR

CROSS REFERENCE TO RELATED APPLICATION

This application is a continuation-in-part of U.S. patent application Ser. No. 08/500,235 filed Jul. 10, 1995, now U.S. Pat. No. 5,568,126.

BACKGROUND OF THE INVENTION

The present invention pertains to personal-security alarm systems and methods such as may be used for detecting and/or deterring an assault, such as a bank robbery.

Typical personal-security alarm systems include an alarm device that is activated by a person being assaulted. The alarm may be an audio alarm that is so loud as to cause the perpetrator of the assault to flee before others respond to the sound of the alarm and/or to escape discomfort caused by the loud alarm. Audio alarms are provided by both small, personally carried alarm devices and by larger alarm systems installed in buildings, such as banks. Alarm systems installed in banks also provide visual, silent alarm indications to locations that are remote from the location of the person activating the alarm, such as a teller window, so that persons viewing the alarm indication may assist in deterring the assault before the perpetrator becomes aware that an alarm indication has been provided. Alarm systems installed in banks also provide audio alarms that are sounded in areas that are remote from the public pan of the bank in order to summon remotely stationed security personnel to the public pan of the bank. Many bank robbers are aware of such alarm systems and frequently prevent a person under assault from activating an alarm.

SUMMARY OF THE INVENTION

The present invention provides a system for providing an alarm when a person suddenly experiences fear, comprising monitoring means for coupling to a person for monitoring at least one physiological condition of the person to provide physiological data signal(s) that are indicative of the status of the monitored physiological condition(s); a computer system coupled to the monitoring means for processing the physiological data signal(s) to determine whether the person may have suddenly experienced fear; and alarm-indicating means coupled to the computer system for providing an alarm indication in response to a determination by said processing that the person may have suddenly experienced fear; wherein the computer system determines whether the person may have suddenly experienced fear by processing the physiological data signal(s) in relation to (1) stored data for the person based upon measurements of the monitored physiological condition(s) of the person during situations of stress and/or (2) stored stress profile data based upon statistical classification in view of a combination of predetermined characteristics of the person.

The present invention also provides a system for detecting and/or deterring an assault, such as a bank robbery, at a facility, such as a bank, comprising monitoring means for coupling to a person, such as a bank teller, for monitoring at least one physiological condition of the person to provide physiological data signal(s) that are indicative of the status of the monitored physiological condition(s); a computer system coupled to the monitoring means for processing the physiological data signal(s) to determine whether the person may have suddenly experienced fear; and alarm-indicating means coupled to the computer system for providing an alarm indication in response to a determination by said processing that the person may have suddenly experienced fear; wherein the alarm-indicating means are so adapted and/or disposed at the facility as to provide an initial alarm indication that is perceivable by the person whose physiological condition is monitored but is not perceivable by a perpetrator of said assault.

The present invention further provides a system for providing an alarm when a person suddenly experiences fear, comprising monitoring means for coupling to a person for monitoring at least one physiological condition of the person to provide physiological data signal(s) that are indicative of the status of the monitored physiological condition(s); a computer system coupled to the monitoring means for processing the physiological data signal(s) to determine whether the person may have suddenly experienced fear; first alarm-indicating means coupled to the computer system for providing a first alarm indication in response to a determination by said processing that the person may have suddenly experienced fear; means for providing an alarm-deactivation signal that causes the computer system to deactivate the first alarm-indicating means; and means for manually activating a second alarm indication.

The present invention additionally provides a system for providing an alarm when a person suddenly experiences fear, comprising monitoring means for coupling to a person for monitoring at least one physiological condition of the person to provide physiological data signal(s) that are indicative of the status of the monitored physiological condition(s); a computer system coupled to the monitoring means for processing the physiological data signal(s) to determine whether the person may have suddenly experienced fear; alarm-indicating means coupled to the computer system for providing an alarm indication in response to a determination by said processing that the person may have suddenly experienced fear; and recording means disposed relative to the monitoring means for recording given conditions at the site of said person, including said given conditions extant both prior to and after any said determination by said processing that the person may have suddenly experienced fear.

The present invention still also provides a system for providing an alarm when a person suddenly experiences fear, comprising monitoring means for coupling to a person for monitoring at least one physiological condition of the person to provide physiological data signal(s) that are indicative of the status of the monitored physiological condition(s); a computer system coupled to the monitoring means for processing the physiological data signal(s) to determine whether the person may have suddenly experienced fear; alarm-indicating means coupled to the computer system for providing an alarm indication in response to a determination by said processing that the person may have suddenly experienced fear; and recording means disposed relative to the monitoring means for recording given conditions at the site of said person, and coupled to the computer system for being activated to record said given conditions in response to said determination.

The present invention sill further provides a system for providing an alarm when a person suddenly experiences fear, comprising monitoring means for coupling to a person for monitoring at least one physiological condition of the person to provide physiological data signal(s) that are indicative of the status of the monitored physiological condition(s); a computer system coupled to the monitoring means for processing the physiological data signal(s) to determine whether the person may have suddenly experienced fear; alarm-indicating means coupled to the computer system for providing an alarm indication in response to a determination by said processing that the person may have suddenly experienced fear; and communication means disposed relative to the monitoring means for transmitting to a remote location signals indicating given conditions at the site of said person, and coupled to the monitoring means for being activated to transmit said given-conditions-indicating signals in response to said determination. The present invention still additionally provides a system for providing an alarm when a person suddenly experiences fear, comprising monitoring means for coupling to a person for monitoring at least one physiological condition of the person to provide physiological data signal(s) that are indicative of the status of the monitored physiological condition(s); a computer system coupled to the monitoring means for processing the physiological data signal(s) to determine whether the person may have suddenly experienced fear; alarm-indicating means coupled to the computer system for providing an alarm indication in response to a determination by said processing that the person may have suddenly experienced fear; and means for providing an alarm deactivation signal that causes the computer system to deactivate the alarm-indicating means; wherein the alarm-indicating means are so adapted and/or disposed as to provide an initial alarm indication that is perceivable by the person to whom the monitoring means are coupled; wherein the initial alarm indication commences shortly after said determination and the alarm-indicating means further includes a second alarm-indicating means that is so coupled to the computer system as to commence a second alarm indication a given interval after commencement of the initial alarm indication if the alarm-indicating means is not deactivated within said given interval following commencement of the initial alarm indication; and wherein the computer system determines the duration of said given interval in accordance with predetermined characteristics of the physiological data signal(s) processed by the computer system.

In another aspect, the present invention provides a system for determining when a person suddenly experiences fear, comprising monitoring means for coupling to a person for monitoring at least one physiological condition of the person provide physiological data signal(s) that are indicative of the status of the monitored physiological condition(s); and a computer system coupled to the monitoring means for processing the physiological data signal(s) to determine whether the person may have suddenly experienced fear by processing the physiological data signal(s) in relation to stored stress-profile data for the person based upon measurements of the monitored physiological condition(s) of the person during situations of stress.

The present invention further provides methods corresponding to the above-described systems.

Additional features of the present invention are described with reference to the detailed description of the preferred embodiments.

DETAILED DESCRIPTION

Figure 1:
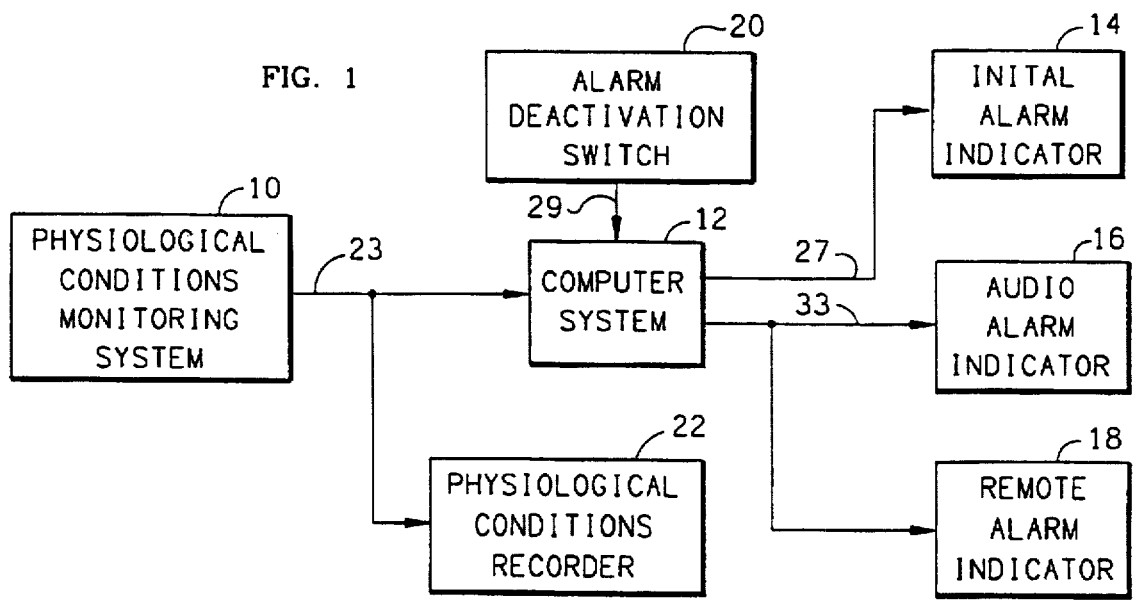
FIG. 1 is a block diagram of one preferred embodiment of a system according to the present invention.

Referring to FIG. 1, a preferred embodiment of a the system according to the present invention includes physiological-conditions monitoring system 10, a computer system 12, an initial alarm indicator 14, an audio alarm indicator 16, an remote alarm indicator 18, an alarm deactivation switch 20, and a physiological-conditions recorder 22.

The physiological-condition monitoring system 10 includes probes for attachment to a person for use in measuring such conditions as pulse rate, skin conductivity and respiration; signal conditioning apparatus and communication apparatus. The signal conditioning apparatus includes a first unit for conditioning the signals provided by the probes for transfer by the communication apparatus. The communication apparatus includes a radio transmitter for transmitting the conditioned probe signals from the monitored person and a radio receiver for receiving the probe signals transmitted by the radio transmitter. The radio receiver is coupled to both the computer 12 and the monitored data recorder 22 for transferring thereto the probe signals received from the radio transmitter. The radio receiver may be coupled to the computer system 12 and/or the monitored data recorder 22 via a communication satellite when the computer system 12 and/or the monitored data recorder 22 is not in the vicinity of the monitored person. The signal conditioning apparatus further includes a second unit for conditioning the signals transferred by the communication apparatus to provide monitored physiological data signals 23 for processing by the computer system 12. The first signal conditioning unit and the radio transmitter are adapted for inconspicuous attachment to or containment in a person's clothing.

The monitored physiological data signals 23 are indicative of the status of the monitored physiological conditions of the person to whom the probes are attached. The monitored physiological data signals 23 are also recorded by the physiological-conditions recorder 22.

Figure 2:
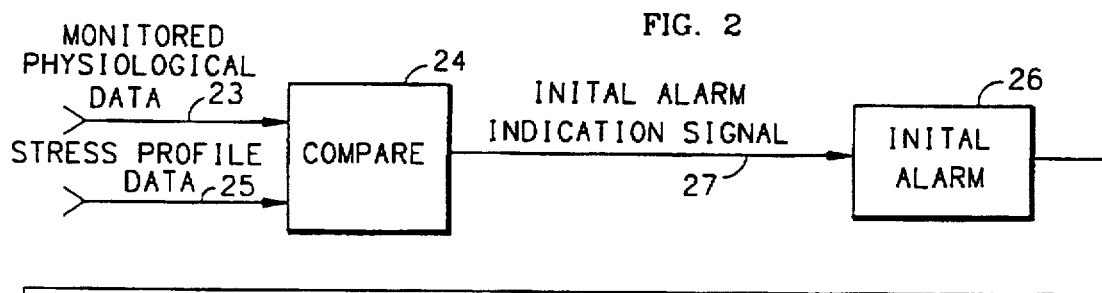
FIG. 2 is a flow diagram illustrating steps performed by the system of FIG. 1 in accordance with the method of the present invention.
Figure 2:
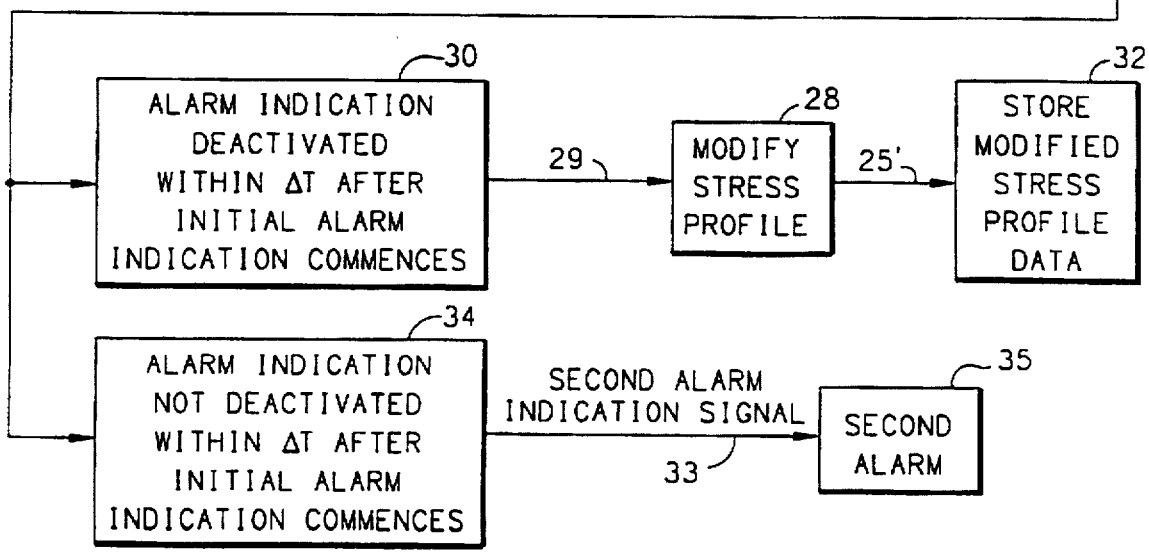

The computer system 12 processes the physiological data signals 23 to determine whether the person may have suddenly experienced fear. Referring to FIG. 2, the computer system 12 determines whether the person may have suddenly experienced fear by the step 24 of comparing the monitored physiological data 23 with stored stress profile data 25 for the person. The stored stress profile data 25 is based upon measurements of the monitored physiological conditions of the person during situations of stress. Alternatively, the stored stress profile data 25 is based upon statistical classification in view of a combination of predetermined characteristics of the person, such as age, gender, family history, medical history and trauma history. In another embodiment, the stored stress profile data 25 is based upon both such a statistical classification and measurements of the monitored physiological conditions of the person during situations of stress. In this embodiment the stress profile data 25 is initially based upon such statistical classification and subsequently is modified as necessary in accordance with the measurements of the monitored physiological conditions of the person during situations of stress.

When such processing step 24 by the computer system 12 of comparing the monitored physiological data signals 23 with stored stress profile data 25 for the person determines that the person may have suddenly experienced fear, the computer system 12 provides an alarm-indication signal 27 to the initial alarm indicator 14.

The initial alarm indicator 14 is activated for providing an initial alarm indication 26 in response to the initial alarm indication signal 27 only while the alarm indication signal 27 remains active. Operation of the alarm deactivation switch 20 causes the computer to discontinue the initial alarm indication signal 27 to thereby deactivate the initial alarm indication 26 by the initial alarm indicator 14.

The initial alarm indicator 14 is so adapted and/or disposed as to provide an initial alarm indication 26 that is perceivable by the person to whom the monitoring system 12 is coupled so that, if the initial alarm indication 26 was false or if the condition causing the person to suddenly experience fear was very brief and no longer poses a threat, the person can operate the alarm deactivation switch 20 to cause the computer system 12 to discontinue the alarm indication signal 27 and thereby deactivate the initial alarm indication 26 by the initial alarm indicator 14 before other persons are alerted to the initial alarm indication 26 and become concerned.

Preferably the initial alarm 26 is a visual alarm, such as provided by a display device or a lamp. Alternatively, or additionally, the initial alarm indication 26 includes an audio alarm sounded by an earplug speaker inserted in the person's ear or a vibration applied to the person's skin by a vibrator attached to the person's body. The speaker and/or the vibrator is activated in response to receipt of the initial alarm indication signal 27 from the computer system 12 by a radio receiver contained in or attached to the person's clothing.

The computer system 12 includes a neural network for modifying the stored stress profile data, as shown by 28 in FIG. 2, in response to an input signal indicating that the computer system 12 provided a false alarm indication. Such an input signal 29 is provided when the alarm deactivation switch 20 is operated to discontinue the initial alarm indication signal 27 and thereby deactivate the alarm indication 26 within a given interval $\Delta T$ following commencement of the initial alarm indication signal 27, as shown by 30.

The computer system 12 determines the duration of the given interval $\Delta T$ in accordance with predetermined characteristics of the monitored physiological data signals 23 processed by the computer system 12. Such characteristics include the degree of difference between the monitored physiological data 23 and the stored stress profile data 25 with respect to those parameters of the stress profile in which differences are detected during said comparison, with the given interval $\Delta T$ determination being based upon the particular parameters in which differences are detected and the respective degrees of such differences.

The modified stress profile data 25' is stored as shown by 32, for comparison with monitored physiological data 23 subsequently received by the computer system 12.

The initial alarm indication signal 27 commences shortly after the computer system 12 determines that the person may have suddenly experienced fear. If the alarm deactivation switch 20 is not operated within the given interval $\Delta T$ following commencement of the initial alarm indication signal 27 in order to deactivate the initial alarm indication 26, as indicated by 34 in FIG. 2, the computer system 12 provides a second alarm indication signal 33 to the audio alarm indicator 16 and to the remote alarm indicator 18 and thereby causes both audio alarm indicator 16 and the remote alarm indicator 18 to commence alarm indications. The audio alarm indicator 16 provides a second alarm indication 35. The remote alarm indicator 18 provides both visual and audio alarm indications. The audio alarm indicator 16 is so located that the audio alarm provided by the audio alarm indicator 16 is perceivable at the location of the monitored person. The remote alarm indicator 18 is so located that any audio alarm provided by the remote alarm indicator 18 is not perceivable at the location of the monitored person.

Figure 3:
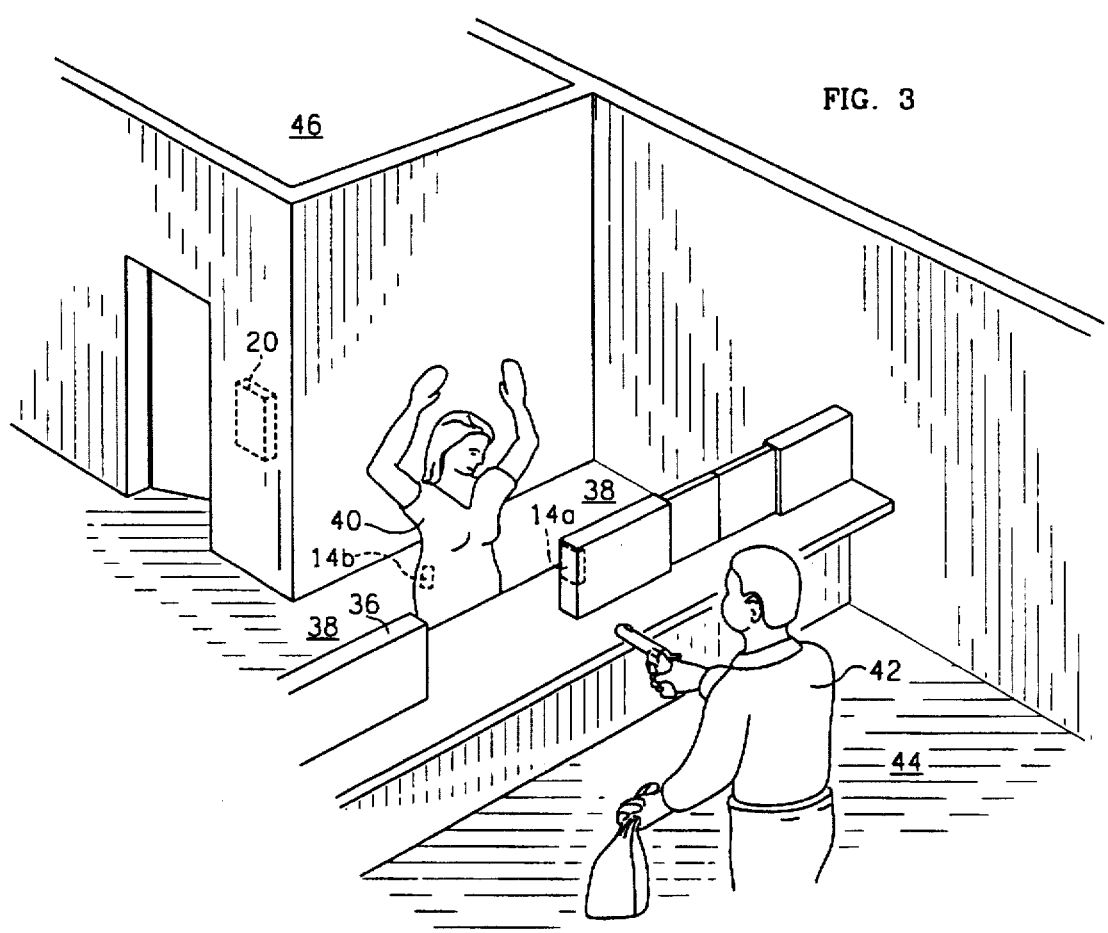
FIG. 3 is a perspective view showing the relative location of a visual alarm indication display and an alarm deactivation switch in an embodiment of the system of FIG. 1.

In an embodiment of the invention adapted for deterring an assault at a facility, such as a bank, the initial alarm indicator 14 is so adapted and/or disposed at the facility as to provide an initial alarm indication that is perceivable by the person whose physiological condition is monitored but is not perceivable by a perpetrator of the assault. Referring to FIG. 3, the initial alarm indicator 14 includes a visual alarm display 14a, which is disposed behind a barrier 36 enclosing a portion of a given area 38 normally occupied by the monitored person 40, such as a bank teller, so as to be obscured from view by a perpetrator, such as a bank robber 42 on the other side of the barrier 36. The initial alarm indicator 14 may additionally or alternatively include an earplug speaker, (not shown) and/or a vibrator 14b, which is attached to the body of the monitored person 40 for activation in response to receipt of the initial alarm indication signal 27 provided by the computer system 12, as described above. The alarm indications provided by the earplug speaker and/or the vibrator 14b are not perceivable by a perpetrator of an assault, such as the bank robber 42.

The alarm deactivation switch 20 is located in an area, such as a separate room 46, of the facility that is remote from the given area 38 normally occupied by the monitored person 40 such that a person within the given area 38 could not operate the alarm deactivation switch 20; thereby preventing the alarm deactivation switch 20 from being operated by, or in response to a command by, a perpetrator of an assault 42 unless the perpetrator 42 either (1) crosses over the barrier 36 and thereby risks alerting other persons, or (2) the perpetrator 42 allows the monitored person 40 to leave the perpetrator's presence by entering the separate room 46 where the alarm deactivation switch 20 is located.

The second alarm indication 35 that is provided if the alarm deactivation switch 20 is not operated within the given interval $\Delta T$ following commencement of the initial alarm indication signal 27 in order to deactivate the initial alarm indication 26 includes an audio alarm provided by the audio alarm indicator 16 and/or the remote alarm indicator 18. The second alarm indication 35 may also be manifested by the opening of a trap door located in an area 44 next to the teller window on the side of the barrier 36 occupied by the perpetrator 42.

Figure 4:
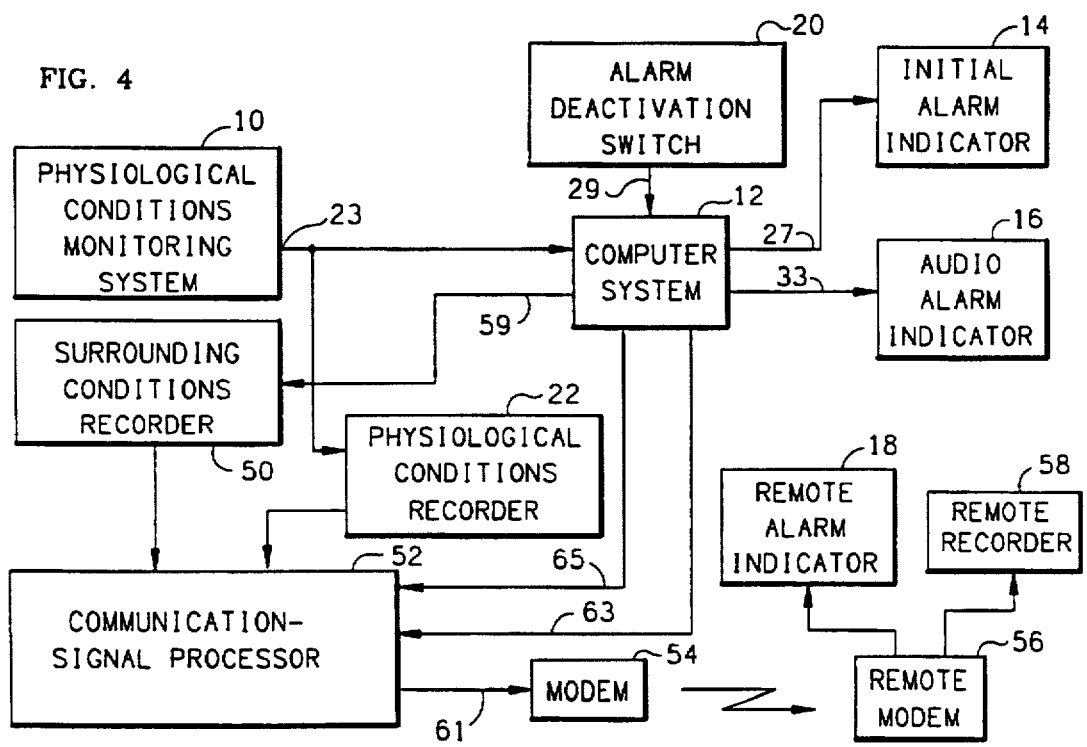
FIG. 4 is a block diagram of another preferred embodiment of a system according to the present invention.

Referring to FIG. 4, another preferred embodiment of a system according to the present invention includes physiological-conditions monitoring system 10, a computer system 12, an initial alarm indicator 14, an audio alarm indicator 16, an remote alarm indicator 18, an alarm deactivation switch 20, and a physiological-conditions recorder 22, such as described above with reference to FIGS. 1 and 2, and also a surrounding conditions recorder 50, a communication signal processor 52, a first modem 54, a remote modem 56 and a remote recorder 58. Except for the remote components 18, 56, 58, the system of this embodiment is adapted to be transported with a person when traveling away from a stationary facility, such as when traveling in an automobile, truck, boat or other conveyance so that should such person encounter conditions that cause him to experience fear, an alarm indication can be provided locally and/or at a remote location and the surrounding conditions that may have caused such fear can be recorded and/or transmitted to a remote location. The system of FIG. 4 can also be used at a stationary facility.

The surrounding conditions recorder 50 is disposed relative to the physiological conditions monitoring system 10 for recording given conditions at the site of the monitored person, including conditions extant both prior to and after any determination by the processing performed by the computer system 12 that the person may have suddenly experienced fear. The surrounding conditions recorder 50 includes a closed loop recording tape upon which the surrounding conditions are recorded continuously, and the recorder is adapted to cease recording in response to a signal 59 from the computer system 22 that is provided a predetermined duration after such a determination that the person may have suddenly experienced fear if the alarm deactivation switch 20 is not operated prior to the end of such predetermined duration. This predetermined duration is longer than the given interval ΔT between the commencement of the initial alarm indication signal 27 and the provision of the second alarm indication signal 33 described above with reference to FIG. 2 so as to enable the surrounding conditions to be recorded for several minutes following the initial alarm indication 26.

The communication signal processor 52 is coupled to the surrounding conditions recorder 50 and the physiological conditions recorder 22 for transmitting a record 61 of the recorded surrounding conditions and/or of the monitored physiological conditions to a remote location via the modems 54, 56 in response to a signal 63 that is provided by the computer system 12 when the processing performed by the computer system 12 determines that the person may have suddenly experienced fear. The modems 54, 56 may be linked for microwave and/or wired communications.

Preferably, the communication signal processor 52 is coupled to the surrounding conditions recorder 50 and the physiological conditions recorder 22 for transmitting the record 61 of the recorded surrounding conditions and/or of the monitored physiological conditions to the remote location as such conditions are being recorded. If the alarm deactivation switch 20 is operated within the given interval ΔT following the commencement of the initial alarm indication signal 27, the computer system 12 provides a signal 65 to the communication signal processor 52 that causes the transmission of the record 61 to be terminated.

The remote alarm indicator 18 provides an alarm indication if the transmission of the record 61 is not terminated within the given interval ΔT following commencement of receipt by the remote modem 56 of the record 61 from the communication signal processor 52. The entire record 61 received from the communication signal processor 52 by the remote modem 56 is recorded by the remote recorder 58.

In one preferred embodiment, which is described with reference to FIG. 1, the alarm deactivation switch 20 is adapted for activating the remote alarm indicator 18 by manually operating the alarm deactivation switch 20 in a manner that is different but may not appear to an observer to be different from the manner in which the alarm deactivation switch 20 is operated to provide the alarm-deactivation signal 29. Whether or not operation of the alarm deactivation switch 20 results in provision of the alarm-deactivation signal 29 or a signal for activating the remote alarm indicator 18 is dependent upon coded operation of the alarm deactivation switch 20. For example, the alarm deactivation switch 20 may be a push-button momentary-contact switch that is pushed for different durations or a different number of times in quick succession to indicate whether the signal provided by operation of the alarm deactivation switch 20 is an alarm-deactivation signal 29 and/or a signal for activating the remote alarm indicator 18. The computer system 12 processes the signal provided by operation of the alarm deactivation switch 20 to determine whether the provided signal is an alarm-deactivation signal 29 and/or a signal for activating the remote alarm indicator 18. The computer system 12 responds to such determination by discontinuing the alarm-indication signal 27 to thereby deactivate the initial alarm indicator 14 and/or by providing the second alarm activation signal 33 to activate the remote alarm indicator 18. This embodiment is particularly useful for deceiving a perpetrator of an assault upon the person being monitored into a sense of false security when the perpetrator has sensed the initial alarm indication, by making the perpetrator believe that operation of the alarm deactivation switch 20 has eliminated any and all alarms.

The advantages specifically stated herein do not necessarily apply to every conceivable embodiment of the present invention. Further, such stated advantages of the present invention are only examples and should not be construed as the only advantages of the present invention.

While the above description contains many specificities, these should not be construed as limitations on the scope of the present invention, but rather as examples of the preferred embodiments described herein. Other variations are possible and the scope of the present invention should be determined not by the embodiments described herein but rather by the claims and their legal equivalents.

We claim:

1. A system for providing an alarm when a person suddenly experiences fear, comprising monitoring means for coupling to a person for monitoring at least one physiological condition of the person to provide physiological data signal(s) that are indicative of the status of the monitored physiological condition(s);

a computer system coupled to the monitoring means for processing the physiological data signal(s) to determine the person may have suddenly experienced fear; and alarm-indicating means coupled to the computer system for providing an alarm indication in response to a determination by said processing that the person may have suddenly experienced fear;

means for providing an alarm deactivation signal causes the computer system to deactivate the alarm indicating means; and means for manually activating a second alarm indication;

wherein the computer system determines whether the person may have suddenly experienced fear by processing the physiological data signal(s) in relation to stored data for the person based upon measurements of the monitored physiological condition(s) of the person during situations of stress.

2. A system according to claim 1, wherein the means for providing the alarm-deactivation signal is adapted for activating the second alarm indicating means by manually operating the means for providing the alarm-deactivation signal in a manner that is different but may not appear to an observer to be different from the manner in which the means for providing the alarm-deactivation signal is operated to provide the alarm-deactivation signal.

3. A system according to claim 1, wherein the means for providing the alarm-deactivation signal is adapted for activating the second alarm indicating means, with provision of the alarm-deactivation signal and/or activation of the second alarm indicating means being dependent upon coded operation of the means for providing the alarm-deactivation signal.

4. A system for providing an alarm when a person suddenly experiences fear, comprising;

monitoring means for coupling to a person fix monitoring at least one physiological condition of the person to provide physiological data signal(s) that are indicative of the status of the monitored physiological condition (s);

a computer system coupled to the monitoring means for processing the physiological data signal(s) to determine whether the person may have suddenly experienced fear;

first alarm-indicating means coupled to the computer system for providing a first alarm indication in response to a determination by said processing that the person may have suddenly experienced fear;

means for providing an alarm-deactivation signal that causes the computer system to deactivate the first alarm-indicating means; and means for manually activating a second alarm indication.

5. A system according to claim 4, wherein the means for providing the alarm-deactivation signal is adapted for activating the second alarm indicating means by manually operating the means for providing the alarm-deactivation signal in a manner that is different but may not appear to an observer to be different from the manner in which the means for providing the alarm-deactivation signal is operated to provide the alarm-deactivation signal.

6. A system according to claim 4, wherein the means for providing the alarm-deactivation signal is adapted for activating the second alarm indicating means, with provision of the alarm-deactivation signal and/or activation of the second alarm indicating means being dependent upon coded operation of the means for providing the alarm-deactivation signal.

7. A system for determining when a person suddenly experiences fear, comprising monitoring means for coupling to a person for monitoring at least one physiological condition of the person provide physiological data signal(s) that are indicative of the status of the monitored physiological condition (s); and a computer system coupled to the monitoring means for processing the physiological data signal(s) to determine whether the person may have suddenly experienced fear by processing the physiological data signal(s) in relation to stored stress-profile data for the person based upon measurements of the monitored physiological condition(s) of the person during situations of stress.

8. A system according to claim 7, wherein the computer system is adapted for modifying said stored stress-profile data in response to an input signal indicating that said processing falsely determined that the person may have suddenly experienced fear.

9. A method of providing an alarm when a person suddenly experiences fear, comprising the steps of:

(a) monitoring at least one physiological condition of the person to provide physiological data signal(s) that are indicative of the status of the monitored physiological condition(s);

(b) processing the physiological data signal(s) with a computer system to determine whether the person max, have suddenly experienced fear;

(c) providing an alarm indication in response to a determination by said processing that the person may have suddenly experienced fear;

(d) providing an alarm deactivation signal that causes the computer system to deactivate the alarm-indicating means; and (e) manually activating a second alarm indication;

wherein step (b) includes the step of:

(f) determining whether the person may have suddenly experienced fear by processing the physiological data signal(s) in relation to stored data for the person based upon measurements of the monitored physiological condition(s) of the person during situations of stress.

10. A method according to claim 9, wherein steps (d) and (e) comprise operating a common means that is adapted for providing the alarm-deactivation signal and for activating the second alarm indication, with the provision of steps (d) and/or (e) being dependent upon coded operation of the common means.

11. A method of providing an alarm when a person suddenly experiences fear, comprising the steps of:

(a) monitoring at least one physiological condition of the person to provide physiological data signal(s) that are indicative of the status of the monitored physiological condition(s);

(b) processing the physiological data signal(s) with a computer system to determine whether the person may have suddenly experienced fear;

(c) providing a first alarm indication in response to a determination by said processing that the person may have suddenly experienced fear; and (d) providing an alarm-deactivation signal that causes the computer system to deactivate the first alarm indication; and/or (e) subsequent to step (c), manually activating a second alarm indication.

12. A method according to claim 11, wherein step (e) comprises manually operating means for providing the alarm-deactivation signal in a manner that is different but may not appear to an observer to be different from the manner in which the means providing the alarm-deactivation signal is operated to provide the alarm-deactivation signal.

13. A method according to claim 12, wherein steps (d) and (e) comprise operating a common means that is adapted for providing the alarm-deactivation signal and for activating the second alarm indication, with the provision of steps (d) and/or (e) being dependent upon coded operation of the common means.

14. A method according to claim 11, wherein steps (d) and (e) comprise operating a common means that is adapted for providing the alarm-deactivation signal and for activating the second alarm indication, with the provision of steps (d) and/or (e) being dependent upon coded operation of the common means.

15. A method of determining when a person suddenly experiences fear, comprising the steps of:

(a) monitoring at least one physiological condition of the person to provide physiological data signal(s) that are indicative of the status of the monitored physiological condition(s); and (b) processing the physiological data signal(s) with a computer system to determine whether the person may have suddenly experienced fear by processing the physiological data signal(s) in relation to stored stress-profile data for the person based upon measurements of the monitored physiological condition(s) of the person during situations of stress.

16. A method according to claim 15, further comprising the step of:

(c) modifying said stored stress-profile data in response to an input signal indicating that said processing falsely determined that the person may have suddenly experienced fear.

17. A system for detecting and/or deterring an assault, such as a bank robbery, at a facility, such as a bank, comprising monitoring means for coupling to a person, such as a bank teller, for monitoring at least one physiological condition of the person to provide physiological data signal(s) that are indicative of the status of the monitored physiological condition(s);

a computer system coupled to the monitoring means for processing the physiological data signal(s) to determine whether the person may have suddenly experienced fear; and alarm-indicating means coupled to the computer system for providing an alarm indication in response to a determination by said processing that the person may have suddenly experienced fear;

means for providing an alarm deactivation signal that causes the computer system to deactivate the alarm-indicating means; and means for manually activating a second alarm indication;

wherein the alarm-indicating means are so adapted and/or disposed at the facility as to provide an initial alarm indication that is perceivable by the person whose physiological condition is monitored but is not perceivable by a perpetrator of said assault.

18. A system according to claim 17, wherein the means for providing the alarm-deactivation signal is adapted for activating the second alarm indicating means by manually operating the means for providing the alarm-deactivation signal in a manner that is different but may not appear to an observer to be different from the manner in which the means for providing the alarm-deactivation signal is operated to provide the alarm-deactivation signal.

19. A system according to claim 17, wherein the means for providing the alarm-deactivation signal is adapted for activating the second alarm indicating means, with provision of the alarm-deactivation signal and/or activation of the second alarm indicating means being dependent upon coded operation of the means for providing the alarm-deactivation signal.

20. A method of detecting and/or deterring an assault, such as a bank robbery, comprising the steps of (a) monitoring at least one physiological condition of a person, such as a bank teller, to provide physiological data signal(s) that are indicative of the status of the monitored physiological condition(s);

(b) processing the physiological data signal(s) with a computer system to determine whether the person may have suddenly experienced fear;

(c) providing an alarm indication in response to a determination by said processing that the person may have suddenly experienced fear;

(d) providing an alarm-deactivation signal that causes the computer system to deactivate the above-recited alarm indication; and (e) manually activating a second alarm indication. wherein step (c) includes the step of (f) providing an initial alarm indication that is perceivable by the person whose physiological condition is monitored but is not perceivable by a perpetrator of said assault.

21. A method according to claim 20, wherein step (e) comprises manually operating means for providing the alarm-deactivation signal in a manner that is different but may not appear to an observer to be different from the manner in which the means for providing the alarm-deactivation signal is operated to provide the alarm-deactivation signal.

22. A method according to claim 21, wherein steps (d) and (e) comprise operating a common means that is adapted for providing the alarm-deactivation signal and for activating the second alarm indication, with the provision of steps (d) and/or (e) being dependent upon coded operation of the common means.

23. A method according to claim 20, wherein steps (d) and (e) comprise operating a common means that is adapted for providing the alarm-deactivation signal and for activating the second alarm indication, with the provision of steps (d) and/or (e) being dependent upon coded operation of the common means.

* * * * *

UNITED STATES PATENT AND TRADEMARK OFFICE
CERTIFICATE OF CORRECTION

PATENT NO : 5,745,034
DATED : April 28, 1998
INVENTOR(S): STIG LUNDEGAARD ANDERSEN ET AL.

It is certified that error appears in the above-identified patent and that said Letters Patent is hereby corrected as shown below:

Column 1, line 31, "pan" should read --part--.

Column 1, line 33, "pan" should read --part--.

Column 8, line 43, after "signal", --that-- should be inserted.

Column 9, line 3, "fix" should read --for--.

Signed and Sealed this

Sixth Day of October, 1998

*Attest:*

BRUCE LEHMAN

*Attesting Officer*          *Commissioner of Patents and Trademarks*